US009320300B2

(12) United States Patent
Hon

(10) Patent No.: US 9,320,300 B2
(45) Date of Patent: *Apr. 26, 2016

(54) ELECTRONIC CIGARETTE

(71) Applicant: Fontem Holdings 1 B.V., Amsterdam (NL)

(72) Inventor: Lik Hon, North Point (HK)

(73) Assignee: Fontem Holdings 1 B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,663

(22) Filed: Jun. 18, 2014

(65) Prior Publication Data

US 2014/0305453 A1 Oct. 16, 2014

Related U.S. Application Data

(63) Continuation of application No. 13/208,257, filed on Aug. 11, 2011, now abandoned, which is a continuation of application No. PCT/CN2010/000125, filed on Jan. 28, 2010.

(30) Foreign Application Priority Data

Feb. 11, 2009 (CN) .......................... 2009 2 0001296

(51) Int. Cl.
*A24F 13/00* (2006.01)
*A24F 17/00* (2006.01)
(Continued)

(52) U.S. Cl.
CPC ............ *A24F 47/008* (2013.01); *A61M 11/041* (2013.01); *A61M 11/042* (2014.02); *A61M 15/06* (2013.01); *A61M 2016/0024* (2013.01); *A61M 2205/8206* (2013.01)

(58) Field of Classification Search
None
See application file for complete search history.

(56) References Cited

U.S. PATENT DOCUMENTS 1,775,947 A 9/1930 Robinson
2,057,353 A 10/1936 Whittemore
(Continued)

FOREIGN PATENT DOCUMENTS

AU 2005232354 B2 10/2005
CN 2047485 U 11/1989
(Continued)

OTHER PUBLICATIONS

Njoy, Inc. et al., Defendants' Joint Invalidity Contentions, Case No. CV-14-01645 etc., Aug. 7, 2014.
(Continued)

*Primary Examiner* — Michael H Wilson
*Assistant Examiner* — Phu Nguyen
(74) *Attorney, Agent, or Firm* — Perkins Coie LLP

(57) ABSTRACT

An electronic cigarette has a power device (1), a sensor (2), an atomizing core component and a liquid storage component (3). The atomizing core component includes an electric heater (5) and a liquid permeating component (6). The electric heater (5) has a through hole (51), the liquid storage component (3) has a channel (31), and the sensor (2) is connected with the through hole (51) and the channel (31) to form an airflow loop by the auxiliary air inlet. The liquid permeating component (6) is directly sleeved on the electric heater (5), so that the cigarette can adequately heat gasified smoke with uniform small drops. The electric heater (5) and the liquid storage component (3) are connected with the through hole (51) and the channel (31), so that the vapor generated by the atomizing process can be cooled.

16 Claims, 2 Drawing Sheets

8 1 4 2 10 11 12 7 71 8' 31 3 5 a 13 101 9 6

(51) Int. Cl.

| | |
|---|---|
| ***A24F 25/00*** | (2006.01) |
| ***A24F 47/00*** | (2006.01) |
| ***A61M 11/04*** | (2006.01) |
| ***A61M 15/06*** | (2006.01) |
| *A61M 16/00* | (2006.01) |

(56) References Cited

U.S. PATENT DOCUMENTS 2,631,219 A 3/1953 Suchy
3,200,819 A 8/1965 Gilbert
3,551,643 A 12/1970 Pricenski et al.
4,171,000 A 10/1979 Uhle
4,207,457 A 6/1980 Haglund et al.
4,228,925 A 10/1980 Mendelovich
4,641,053 A 2/1987 Takeda
4,735,217 A 4/1988 Gerth et al.
4,756,318 A 7/1988 Clearman et al.
4,771,796 A 9/1988 Myer
4,819,665 A 4/1989 Roberts et al.
4,848,374 A 7/1989 Chard et al.
4,922,901 A 5/1990 Brooks
4,945,929 A 8/1990 Egilmex
4,945,931 A 8/1990 Gori
4,947,874 A 8/1990 Brooks
4,947,875 A 8/1990 Brooks et al.
4,981,522 A 1/1991 Nichols et al.
5,042,470 A 8/1991 Kanesaka
5,060,671 A 10/1991 Counts et al.
5,080,114 A 1/1992 Rudolph et al.
5,095,921 A 3/1992 Losee et al.
5,144,962 A 9/1992 Counts et al.
5,159,940 A 11/1992 Hayward et al.
5,190,060 A 3/1993 Gerding et al.
5,224,498 A 7/1993 Deevi et al.
5,249,586 A 10/1993 Morgan et al.
5,261,424 A 11/1993 Sprinkel, Jr.
5,285,798 A 2/1994 Banerjee et al.
5,322,075 A 6/1994 Deevi et al.
5,388,594 A 2/1995 Counts et al.
5,438,978 A 8/1995 Hardester, III
5,497,791 A 3/1996 Bowen et al.
5,505,214 A 4/1996 Collins et al.
5,591,368 A 1/1997 Fleischhauer et al.
5,666,977 A 9/1997 Higgins et al.
5,666,978 A 9/1997 Counts et al.
5,730,158 A 3/1998 Collins et al.
5,743,251 A 4/1998 Howell et al.
5,746,251 A 5/1998 Bullard
5,799,663 A 9/1998 Gross et al.
5,819,756 A 10/1998 Mielordt
5,878,752 A 3/1999 Adams et al.
5,894,841 A 4/1999 Voges
6,040,560 A 3/2000 Fleischhauer et al.
6,041,789 A 3/2000 Bankert et al.
6,095,153 A 8/2000 Kessler et al.
6,164,287 A 12/2000 White
6,178,969 B1 1/2001 St. Charles
6,196,218 B1 3/2001 Voges
6,354,293 B1 3/2002 Madison
6,357,671 B1 3/2002 Cewers
6,443,146 B1 9/2002 Voges
6,532,965 B1 3/2003 Abhulimen et al.
6,601,776 B1 8/2003 Oljaca et al.
6,715,494 B1 4/2004 McCoy
6,772,756 B2 8/2004 Shayan
6,803,545 B2 10/2004 Blake et al.
6,810,883 B2 11/2004 Felter et al.
6,854,461 B2 2/2005 Nichols et al.
6,854,470 B1 2/2005 Pu
7,100,618 B2 9/2006 Dominguez
7,131,599 B2 11/2006 Katase
7,726,320 B2 6/2010 Robinson et al.
7,832,410 B2 11/2010 Hon
7,845,359 B2 12/2010 Montaser
7,997,280 B2 8/2011 Rosenthal
8,156,944 B2 4/2012 Han
8,511,318 B2 8/2013 Hon
2003/0108342 A1 6/2003 Sherwood
2004/0089314 A1 5/2004 Felter
2004/0182403 A1 9/2004 Andersson et al.
2004/0261802 A1 12/2004 Griffin et al.
2005/0016550 A1 1/2005 Katase
2005/0236006 A1 10/2005 Cowan
2006/0016453 A1 1/2006 Kim
2006/0191546 A1 8/2006 Takano et al.
2006/0196518 A1 9/2006 Hon
2008/0276947 A1 11/2008 Martzel
2009/0095311 A1 4/2009 Han
2009/0126745 A1 5/2009 Hon
2009/0151717 A1 6/2009 Bowen et al.
2009/0188490 A1* 7/2009 Han ........................ 128/200.14
2009/0230117 A1 9/2009 Fernando et al.
2009/0260642 A1 10/2009 Monsees et al.
2009/0272379 A1 11/2009 Thorens et al.
2010/0031968 A1 2/2010 Sheikh et al.
2010/0126505 A1 5/2010 Rinker
2010/0181387 A1 7/2010 Zaffaroni et al.
2010/0200008 A1 8/2010 Taieb
2010/0242974 A1 9/2010 Pan
2010/0307518 A1 12/2010 Wang
2011/0005535 A1 1/2011 Xiu
2011/0011396 A1 1/2011 Fang
2011/0036346 A1 2/2011 Cohen et al.
2012/0111347 A1 5/2012 Hon

FOREIGN PATENT DOCUMENTS

CN 2084236 U 9/1991
CN 1135860 11/1996
CN 1196660 A 11/1996
CN 7216131 10/1998
CN 1233436 A 11/1999
CN 1252961 A 5/2000
CN 1575673 A 2/2005
CN 2719043 Y 8/2005
CN 200520089947.0 5/2006
CN 200966824 Y * 10/2007
CN 101077225 A 11/2007
CN 20062135072 U 1/2008
CN 201018927 Y 2/2008
CN 201018927 Y 2/2008
CN 20071121524 2/2008
CN 101176805 A 5/2008
CN 201097079 Y 6/2008
CN 201079011 Y 7/2008
CN 201085044 Y 7/2008
CN 201085044 Y 7/2008
CN 2010085044 Y 7/2008
CN 201379072 Y 1/2010
CN 201797997 U 4/2011
CN 2887086 U 11/2011
CN 202026802 U 11/2011
CN 202026804 U 11/2011
DE 10051792 A1 5/2002
DE 102006004484 A1 8/2007
EP 0057243 A1 8/1982
EP 0230420 A1 8/1987
EP 0295122 A2 12/1988
EP 0342538 A2 11/1989
EP 0358002 A2 3/1990
EP 0295122 B1 1/1992
EP 0545186 A2 6/1993
EP 0703735 A1 4/1996
EP 0824927 A2 2/1998
EP 0845220 A1 6/1998
EP 0845220 A1 6/1998
EP 0893071 A1 1/1999
EP 0893071 A1 1/1999
EP 0951219 A1 10/1999
EP 0897271 B1 6/2003
EP 1736065 A1 12/2006
EP 1891867 A2 2/2008
GB 1528391 A 10/1978
JP 64000498 U 1/1989

(56) References Cited

FOREIGN PATENT DOCUMENTS

| | | | |
|---|---|---|---|
| JP | 06114105 | A | 4/1994 |
| JP | 07506999 | | 8/1995 |
| JP | 09075058 | A | 3/1997 |
| UA | 47514 | | 12/1997 |
| WO | WO-9409842 | A1 | 5/1994 |
| WO | WO-9421317 | A1 | 9/1994 |
| WO | WO-9740876 | A2 | 11/1997 |
| WO | WO-9748293 | A1 | 12/1997 |
| WO | WO-9817130 | A1 | 4/1998 |
| WO | 9823171 | A1 | 6/1998 |
| WO | 0028843 | A1 | 5/2000 |
| WO | WO-0049901 | A2 | 8/2000 |
| WO | WO-0105459 | A1 | 1/2001 |
| WO | WO03034847 | | 1/2003 |
| WO | WO-03022364 | | 3/2003 |
| WO | WO-03055486 | | 7/2003 |
| WO | WO03101454 | | 12/2003 |
| WO | WO-04001407 | | 12/2003 |
| WO | WO-2004023222 | | 3/2004 |
| WO | WO-2004080216 | | 9/2004 |
| WO | 2004089126 | A | 10/2004 |
| WO | WO-2005099494 | | 10/2005 |
| WO | WO-2006082571 | | 8/2006 |
| WO | 2007131449 | A | 7/2007 |
| WO | WO-2007078273 | | 7/2007 |
| WO | 2007131449 | | 11/2007 |
| WO | WO-2008077271 | | 7/2008 |
| WO | WO-2008130813 | | 10/2008 |
| WO | WO-2009118085 | | 10/2009 |
| WO | WO-2009135729 | | 11/2009 |
| WO | WO-2010052323 | | 5/2010 |
| WO | WO-2010145468 | | 12/2010 |
| WO | WO-2010145805 | | 12/2010 |
| WO | WO-2011010334 | | 1/2011 |
| WO | WO-2011022431 | | 2/2011 |

OTHER PUBLICATIONS

Njoy, Inc. et al., Attachment E to Defendant's Joint Invalidity Contentions—Claim Charts for Patent 8689805, Aug. 7, 2014.
European Patent Office, Partial European Search Report for EP14155503.7, Sep. 1, 2014.
Anonymous, Third Party Observation for EP Application No. 10740882, Oct. 3, 2013.
Anonymous, Third Party Observations for EP Application No. 100740882, Apr. 11, 2014.
CB Distributors Inc. and DR Distributors, LLC , Petition for Inter Partes Review of US Patent No. 8,156,944 and Exhibits 1-20, filed Jun. 27, 2013.
Chen, Zhiyong—English Translation of Request for Invalidation of CN200620090805.0, Jun. 6, 2013.
*CN Creative and Intellicig USA, Ruyan* v. *Smoking Everywhere* et al. CV11-6268 Invalidity Contentions, Apr. 12, 2012.
CN03111582.9, English Machine Translation corresponding to priority document of Hon '955.
CN200420031182, English Machine Translation corresponding to priority document of Hon '494.
Cyphert Gil DBA NU1S, *Ruyan* v. *Smoking Everywhere* et al. CV11-0367 Invalidity Contentions, Apr. 11, 2012.
Eurasian Patent Office, Official Action for EA 201171031, Jul. 4, 2013.
Eurasian Patent Office, Official Action for EA 201171031, Jul. 2, 2014.
European Patent Office, extended European Search Report for EP07721148, Dec. 6, 2010.
European Patent Office, Supplementary European Search Report and Search Opinion for EP 10740882.5, Oct. 16, 2013.
European Patent Office, extended European Search Report for EP11001479, Jul. 4, 2011.
European Patent Office, Supplemental Extended European Search Report for EP04718242, Jul. 27, 2007.
European Patent Office, Supplemental Partial Extended European Search Report for EP04718242, May 22, 2007.
European Patent Office, Supplementary Extended European Search Report for EP05729107, Jul. 31, 2007.
European Patent Office, Supplementary Partial Extended European Search Report for EP05729107, May 22, 2007.
FIN Branding Group, LLC, Request for Inter Partes Reexamination of U.S. Patent No. 8,156,944, Sep. 13, 2012.
FIN Branding Group, LLC, Third Party Response to Amendment including Submission of Prior Arts and Misc. Statement Per 37 CFR 1.948 and Oljaca 6601776 in Reexamination of U.S. Patent No. 8,156,944, Feb. 27, 2013.
India Patent Office, First Examination Report for in 8528/DELNP/2008, Mar. 27, 2014.
Introduction to selecting and using electronic components, ISBN7-111-13752-3.
IP Australia, Exam Report for AU2004234199, Aug. 14, 2009.
IP Australia, Examination Report for SG 200505930-8, May 4, 206.
IP Australia, Examination Report for SG200604498-6, Apr. 16, 2008.
IP Australia, Patent Examination Report No. 1 for AU2007250367, Jul. 30, 2012.
IP Australia, Patent Examination Report No. 1 for AU2007250368, Aug. 9, 2012.
IP Australia, Patent Examination Report No. 1 for AU 2010213240, Aug. 5, 2013.
Japanese Patent Office, Office Action for JP2006504199, Oct. 30, 2009.
Japanese Patent Office, Office Action for JP2011-549417, Jan. 22, 2014.
Korean Intellectual Property Office, Ntc of Preliminary Rejection for KR1020057009767, Jul. 27, 2009.
Macau Patent Office, Official Communication for MOI121, Apr. 17, 2009.
Malaysian Patent Office, Examination Report for MY PI 20041407, Sep. 28, 2007.
Manual for Electric Engineers, 2nd Ed, Mar. 2000.
Manual for Mechanical Designers, 4th Ed, Jan. 2002.
Materials Manual—Nonmetal, Jul. 1, 1985.
Pan, Fenglin—Request for Invalidation of CN200720148285.9 in Chinese, along with English translation of same.
Pan, Fenglin—Request for Invalidation of CN200920001296.3 in Chinese, along with English translation of same.
*Sottera, Inc., Ruyan* v. *Smoking Everywhere* et al. CV11-0367 Invalidity Contentions Exhibit 7 (Claim 20 Claim Chart), Apr. 12, 2012.
*Sottera, Inc., Ruyan* v. *Smoking Everywhere* et al. CV11-0367 Invalidity Contentions Exhibit 8 (Claim 24 Claim Chart), Apr. 12, 2012.
*Sottera, Inc., Ruyan* v. *Smoking Everywhere* et al. CV11-0367 Invalidity Contentions, Apr. 12, 2012.
State Intellectual Property Office, P.R. China, English translation of Written Opinion for PCT/CN07/001576, Aug. 3, 2007.
State Intellectual Property Office, P.R. China, International Search Report for PCT/CN04/000182, Jun. 10, 2004.
State Intellectual Property Office, P.R. China, International Search Report for PCT/CN05/000337, Jul. 14, 2005.
State Intellectual Property Office, P.R. China, English Translation of Written Opinion for PCT/CN07/001575, Jul. 20, 2007.
State Intellectual Property Office, P.R. China, International Search Report and Written Opinion for PCT/CN10/073613, Aug. 26, 2010.
State Intellectual Property Office, P.R. China, International Search Report for PCT/CN07/001575, Aug. 16, 2007.
State Intellectual Property Office, P.R. China, International Search Report for PCT/CN07/001576, Aug. 16, 2007.
State Intellectual Property Office, P.R. China, International Search Report for PCT/CN10/000125, Apr. 1, 2010.
State Intellectual Property Office, P.R. China, Search Report for Utility Model Patent ZL 200620090805.0, Nov. 18, 2008.
State Intellectual Property Office, P.R. China, Office Action for CN201080016105.6, Dec. 27, 2012) 1st OA), with English translation.
State Intellectual Property Office, P.R. China, Office Action for CN201080016105.6, Aug. 30, 2013 (2nd OA), with English translation.

(56) References Cited

OTHER PUBLICATIONS

State Intellectual Property Office, P.R. China, Office Action for CN201080016105.6, Mar. 13, 2014 (3rd OA), with English translation.

Taiwan Patent Office, Official Letter for TW093111573, Apr. 24, 2009.

TechPowerUp "What is a MOSFET, what does it look like and how does it work?" Dated May 24, 2004; 3 pgs. printed from Internet Jun. 4, 2011.

Ukraine Patent Office, Examination Report for UA200511258, Feb. 4, 2009.

United States Patent and Trademark Office, Office Action in Inter Partes Reexamination, mailed Nov. 27, 2012.

United States Patent and Trademark Office, Office Action for U.S. Appl. No. 13/426,817, mailed Jun. 7, 2013.

United States Patent and Trademark Office, Office Action for U.S. Appl. No. 13/426,817 mailed Jan. 17, 2013.

United States Patent and Trademark Office, Office Action for U.S. Appl. No. 13/208,257 mailed Feb. 4, 2013.

Eurasian Patent Office, Official Action for EA 201171031, Mar. 30, 2015.

European Patent Office, extended European Search Report for EP14155504, Jan. 30, 2015.

Japanese Patent Office, Office Action for JP2011-549417 (2nd OA), Oct. 6, 2014 (with English Translation).

Korean Intellectual Property Office, Notice of Preliminary Rejection for KR10-2011-7021209, Oct. 21, 2014 (with English translation).

State Intellectual Property Office, P.R. China, Decision of Patent Invalidation Petition, CN200920001296.3, Sep. 29, 2014 (with English Translation).

State Intellectual Property Office, Office Action for CN201080016105.6 (5th OA), Mar. 30, 2015, with English Translation.

USPTO Patent Trial and Appeal Board, Institution Decision for IPR2014-01529 (U.S. Pat. No. 8,689,805), Mar. 12, 2015.

CB Distributors, Inc. and DR Distributors, LLC, Petition for Inter Partes Review of U.S. Pat. No. 8,689,805—IPR2014-01529, Paper 2, Sep. 22, 2014.

CB Distributors, Inc. and DR Distributors, LLC, Petition for Inter Partes Review of U.S. Pat. No. 8,689,805—IPR2014-01529, Exhibit 1001, U.S. Pat. No. 8,689,805 to Hon, Sep. 22, 2014.

CB Distributors, Inc. and DR Distributors, LLC, Petition for Inter Partes Review of U.S. Pat. No. 8,689,805—IPR2014-01529, Exhibit 1002, Declaration of Samuel David Piper, P.E., Sep. 22, 2014.

CB Distributors, Inc. and DR Distributors, LLC, Petition for Inter Partes Review of U.S. Pat. No. 8,689,805—IPR2014-01529, Exhibit 1003, Jan. 17, 2013, Office Action, Sep. 22, 2014.

CB Distributors, Inc. and DR Distributors, LLC, Petition for Inter Partes Review of U.S. Pat. No. 8,689,805—IPR2014-01529, Exhibit 1004, China Patent Application No. CN200966824Y to Hon ("Hon '824"), Sep. 22, 2014.

CB Distributors, Inc. and DR Distributors, LLC, Petition for Inter Partes Review of U.S. Pat. No. 8,689,805—IPR2014-01529, Exhibit 1005, Certified English Translation of China Patent Application No. CN200966824Y to Hon, Sep. 22, 2014.

CB Distributors, Inc. and DR Distributors, LLC, Petition for Inter Partes Review of U.S. Pat. No. 8,689,805—IPR2014-01529, Exhibit 1006, Feb. 15, 2013, Response to Office Action, Sep. 22, 2014.

CB Distributors, Inc. and DR Distributors, LLC, Petition for Inter Partes Review of U.S. Pat. No. 8,689,805—IPR2014-01529, Exhibit 1007, Jun. 7, 2013, Final Office Action, Sep. 22, 2014.

CB Distributors, Inc. and DR Distributors, LLC, Petition for Inter Partes Review of U.S. Pat. No. 8,689,805—IPR2014-01529, Exhibit 1008, Sep. 27, 2013, Interview Summary, Sep. 22, 2014.

CB Distributors, Inc. and DR Distributors, LLC, Petition for Inter Partes Review of U.S. Pat. No. 8,689,805—IPR2014-01529, Exhibit 1009, Sep. 13, 2013, Response to Office Action, Sep. 22, 2014.

CB Distributors, Inc. and DR Distributors, LLC, Petition for Inter Partes Review of U.S. Pat. No. 8,689,805—IPR2014-01529, Exhibit 1010, Sep. 13, 2013, Declaration of Lik Hon Under CFR Rule 1.132, Sep. 22, 2014.

CB Distributors, Inc. and DR Distributors, LLC, Petition for Inter Partes Review of U.S. Pat. No. 8,689,805—IPR2014-01529, Exhibit 1011, U.S. Patent Application No. US 2009/0188490 to Hon, Sep. 22, 2014.

CB Distributors, Inc. and DR Distributors, LLC, Petition for Inter Partes Review of U.S. Pat. No. 8,689,805—IPR2014-01529, Exhibit 1012, Dec. 23, 2013, Notice of Allowance and Examiners Amendment, Sep. 22, 2014.

CB Distributors, Inc. and DR Distributors, LLC, Petition for Inter Partes Review of U.S. Pat. No. 8,689,805—IPR2014-01529, Exhibit 1013, China Patent Application No. CN201018927Y to Wang, Sep. 22, 2014.

CB Distributors, Inc. and DR Distributors, LLC, Petition for Inter Partes Review of U.S. Pat. No. 8,689,805—IPR2014-01529, Exhibit 1014, Certified English Translation of China Patent Application No. CN201018927Y to Wang, Sep. 22, 2014.

CB Distributors, Inc. and DR Distributors, LLC, Petition for Inter Partes Review of U.S. Pat. No. 8,689,805—IPR2014-01529, Exhibit 1015, WO 2007/131449 A1 to Hon, Sep. 22, 2014.

CB Distributors, Inc. and DR Distributors, LLC, Petition for Inter Partes Review of U.S. Pat. No. 8,689,805—IPR2014-01529, Exhibit 1016, Certified English Translation of WO 2007/131449 A1 to Hon, Sep. 22, 2014.

CB Distributors, Inc. and DR Distributors, LLC, Petition for Inter Partes Review of U.S. Pat. No. 8,689,805—IPR2014-01529, Exhibit 1017, U.S. Pat. No. 2006/0196518 to Hon, Sep. 22, 2014.

CB Distributors, Inc. and DR Distributors, LLC, Petition for Inter Partes Review of U.S. Pat. No. 8,689,805—IPR2014-01529, Exhibit 1018, WO 2007/078273 A1 to Liu, Sep. 22, 2014.

NJOY, Inc., Petition for Inter Partes Review of U.S. Pat. No. 8,689,805—IPR2015-01027, Paper 2, Apr. 10, 2015.

NJOY, Inc., Petition for Inter Partes Review of U.S. Pat. No. 8,689,805—IPR2015-01027, Exhibit 1001, U.S. Pat. No. 8,689,805 to Hon, Apr. 10, 2015.

NJOY, Inc., Petition for Inter Partes Review of U.S. Pat. No. 8,689,805—IPR2015-01027, Exhibit 1002, Declaration of Samuel David Piper, P.E., Apr. 10, 2015.

NJOY, Inc., Petition for Inter Partes Review of U.S. Pat. No. 8,689,805—IPR2015-01027, Exhibit 1003, Jan. 17, 2013, Office Action, Apr. 10, 2015.

NJOY, Inc., Petition for Inter Partes Review of U.S. Pat. No. 8,689,805—IPR2015-01027, Exhibit 1004, China Patent Application No. CN200966824Y to Hon ("Hon '824"), Apr. 10, 2015.

NJOY, Inc., Petition for Inter Partes Review of U.S. Pat. No. 8,689,805—IPR2015-01027, Exhibit 1005, Certified English Translation of China Patent Application No. CN200966824Y to Hon, Apr. 10, 2015.

NJOY, Inc., Petition for Inter Partes Review of U.S. Pat. No. 8,689,805—IPR2015-01027, Exhibit 1006, Feb. 15, 2013, Response to Office Action, Apr. 10, 2015.

NJOY, Inc., Petition for Inter Partes Review of U.S. Pat. No. 8,689,805—IPR2015-01027, Exhibit 1007, Jun. 7, 2013, Final Office Action, Apr. 10, 2015.

NJOY, Inc., Petition for Inter Partes Review of U.S. Pat. No. 8,689,805—IPR2015-01027, Exhibit 1008, Sep. 27, 2013, Interview Summary, Apr. 10, 2015.

NJOY, Inc., Petition for Inter Partes Review of U.S. Pat. No. 8,689,805—IPR2015-01027, Exhibit 1009, Sep. 13, 2013, Response to Office Action, Apr. 10, 2015.

NJOY, Inc., Petition for Inter Partes Review of U.S. Pat. No. 8,689,805—IPR2015-01027, Exhibit 1010, Sep. 13, 2013, Declaration of Lik Hon Under CFR Rule 1.132, Apr. 10, 2015.

NJOY, Inc., Petition for Inter Partes Review of U.S. Pat. No. 8,689,805—IPR2015-01027, Exhibit 1011, U.S. Patent Application No. US 2009/0188490 to Hon, Apr. 10, 2015.

NJOY, Inc., Petition for Inter Partes Review of U.S. Pat. No. 8,689,805—IPR2015-01027, Exhibit 1012, Dec. 23, 2013, Notice of Allowance and Examiners Amendment, Apr. 10, 2015.

(56) References Cited

OTHER PUBLICATIONS

NJOY, Inc., Petition for Inter Partes Review of U.S. Pat. No. 8,689,805—IPR2015-01027, Exhibit 1013, China Patent Application No. CN201018927Y to Wang, Apr. 10, 2015.
NJOY, Inc., Petition for Inter Partes Review of U.S. Pat. No. 8,689,805—IPR2015-01027, Exhibit 1014, Certified English Translation of China Patent Application No. CN201018927Y to Wang, Apr. 10, 2015.
NJOY, Inc., Petition for Inter Partes Review of U.S. Pat. No. 8,689,805—IPR2015-01027, Exhibit 1015, WO 2007/131449 A1 to Hon, Apr. 10, 2015.
NJOY, Inc., Petition for Inter Partes Review of U.S. Pat. No. 8,689,805—IPR2015-01027, Exhibit 1016, Certified English Translation of WO 2007/131449 A1 to Hon, Apr. 10, 2015.
NJOY, Inc., Petition for Inter Partes Review of U.S. Pat. No. 8,689,805—IPR2015-01027, Exhibit 1017, U.S. Patent Application No. US 2006/0196518 to Hon, Apr. 10, 2015.
NJOY, Inc., Petition for Inter Partes Review of U.S. Pat. No. 8,689,805—IPR2015-01027, Exhibit 1018, WO 2007/078273 A1 to Liu, Apr. 10, 2015.
U.S. Patent and Trademark Office Patent Trial and Appeal Board, IPR2015-01027, Institution Decision, Paper 10, Jun. 5, 2015.
JT International, S.A., Petition for Inter Partes Review of U.S. Pat. No. 8,689,805—IPR2015-01578, Paper 1, Jul. 15, 2015.
JT International, S.A., Petition for Inter Partes Review of U.S. Pat. No. 8,689,805—IPR2015-01578, Exhibit 1001, U.S. Pat. No. 8,689,805 to Hon, Jul. 15, 2015.
JT International, S.A., Petition for Inter Partes Review of U.S. Pat. No. 8,689,805—IPR2015-01578, Exhibit 1002, Declaration of Jeffrey A. Schuster, Ph.D., Jul. 15, 2015.
JT International, S.A., Petition for Inter Partes Review of U.S. Pat. No. 8,689,805—IPR2015-01578, Exhibit 1003, Jan. 17, 2013, Office Action, Jul. 15, 2015.
JT International, S.A., Petition for Inter Partes Review of U.S. Pat. No. 8,689,805—IPR2015-01578, Exhibit 1004, Feb. 15, 2013, Response to Non-Final Office Action, Jul. 15, 2015.
JT International, S.A., Petition for Inter Partes Review of U.S. Pat. No. 8,689,805—IPR2015-01578, Exhibit 1005, Jun. 7, 2013, Final Office Action, Jul. 15, 2015.
JT International, S.A., Petition for Inter Partes Review of U.S. Pat. No. 8,689,805—IPR2015-01578, Exhibit 1006, Sep. 13, 2013, Response to Final Office Action, Jul. 15, 2015.
JT International, S.A., Petition for Inter Partes Review of U.S. Pat. No. 8,689,805—IPR2015-01578, Exhibit 1007, Sep. 13, 2013, Declaration of Lik Hon Under CFR Rule 1.132, Jul. 15, 2015.
JT International, S.A., Petition for Inter Partes Review of U.S. Pat. No. 8,689,805—IPR2015-01578, Exhibit 1008, Sep. 27, 2013, Interview Summary, Jul. 15, 2015.
JT International, S.A., Petition for Inter Partes Review of U.S. Pat. No. 8,689,805—IPR2015-01578, Exhibit 1009, Dec. 23, 2013, Notice of Allowance and Examiner's; Amendment, Jul. 15, 2015.
JT International, S.A., Petition for Inter Partes Review of U.S. Pat. No. 8,689,805—IPR2015-01578, Exhibit 1010, China Patent Application No. CN200966824Y to Hon, Jul. 15, 2015.
JT International, S.A., Petition for Inter Partes Review of U.S. Pat. No. 8,689,805—IPR2015-01578, Exhibit 1011, Certified English Translation of China Patent Application No. CN; 200966824Y to Hon, Jul. 15, 2015.
JT International, S.A., Petition for Inter Partes Review of U.S. Pat. No. 8,689,805—IPR2015-01578, Exhibit 1012, U.S. Patent Application No. US 2009 0188490 to Hon, Jul. 15, 2015.
JT International, S.A., Petition for Inter Partes Review of U.S. Pat. No. 8,689,805—IPR2015-01578, Exhibit 1013, The American Heritage Dictionary ("conduct") ("permeate"), Jul. 15, 2015.
JT International, S.A., Petition for Inter Partes Review of U.S. Pat. No. 8,689,805—IPR2015-01578, Exhibit 1014, Merriam-Webster.com ("sleeve"), Jul. 15, 2015.
JT International, S.A., Petition for Inter Partes Review of U.S. Pat. No. 8,689,805—IPR2015-01578, Exhibit 1015, China Patent Application Publication No. 201085044 Y to Fang, Jul. 15, 2015.
JT International, S.A., Petition for Inter Partes Review of U.S. Pat. No. 8,689,805—IPR2015-01578, Exhibit 1016, Certified English Translation of China Patent Application Publication No. 2010085044 Y to Fang, Jul. 15, 2015.
JT International, S.A., Petition for Inter Partes Review of U.S. Pat. No. 8,689,805—IPR2015-01578, Exhibit 1017, China Patent Application No. CN201018927Y to Wang, Jul. 15, 2015.
JT International, S.A., Petition for Inter Partes Review of U.S. Pat. No. 8,689,805—IPR2015-01578, Exhibit 1018, Certified English Translation of China Patent Application No. CN201018927Y to Wang, Jul. 15, 2015.
JT International, S.A., Petition for Inter Partes Review of U.S. Pat. No. 8,689,805—IPR2015-01578, Exhibit 1019, WO 2007/131449 Al to Hon, Jul. 15, 2015.
JT International, S.A., Petition for Inter Partes Review of U.S. Pat. No. 8,689,805—IPR2015-01578, Exhibit 1020, Certified English Translation of WO 2007/131449 Al to Hon, Jul. 15, 2015.
JT International, S.A., Petition for Inter Partes Review of U.S. Pat. No. 8,689,805—IPR2015-01578, Exhibit 1021, WO 00/28843 A1 to Pienemann, Jul. 15, 2015.
JT International, S.A., Petition for Inter Partes Review of U.S. Pat. No. 8,689,805—IPR2015-01578, Exhibit 1022, Certified English Translation of WO 00/28843 to Pienemann, Jul. 15, 2015.
JT International, S.A., Petition for Inter Partes Review of U.S. Pat. No. 8,689,805—IPR2015-01578, Exhibit 1023, WO 2007/078273 Al to Liu, Jul. 15, 2015.
JT International, S.A., Petition for Inter Partes Review of U.S. Pat. No. 8,689,805—IPR2015-01578, Exhibit 1024, U.S. Pat. No. 4,771,796 to Myer, Jul. 15, 2015.
JT International, S.A., Petition for Inter Partes Review of U.S. Pat. No. 8,689,805—IPR2015-01578, Exhibit 1025, Halliday D., Resnick, R., Physics (Part 2) (1923), Jul. 15, 2015.
JT International, S.A., Petition for Inter Partes Review of U.S. Pat. No. 8,689,805—IPR2015-01578, Exhibit 1026, N. A. Fuchs, The Mechanics of Aerosols (1989), Jul. 15, 2015.
European Patent Office, Notice of Opposition, European Application No. 10740882.5, Sep. 18, 2105.
State Intellectual Property Office, Decision of Rejection for Chinese Application No. 201080016105.6, Jul. 28, 2015.
U.S. District Court, Central District of California, Western Division, Defendant NJOY, Inc.'s Memorandum of Points and Authorities in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 1 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 5 to Defendants' Motion for Leave to

(56) References Cited

OTHER PUBLICATIONS

Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in Consolidated Case No. CV 14-01645 GW (MRW) and related consolidated cases.
U.S. District Court, Central District of California, Western Division, Defendant NJOY, Inc.'s production documents VLACHOS 0000061-72; Consolidated Case No. CV 14-01645 GW (MRW) and related consolidated cases.
Collins, John M., Expert Report—Invalidity (Excerpts), CV14-01645, Jun. 18, 2015.
Collins, John M., Expert Report—Invalidity, CV14-01645-Appendix I-1-'805, Jun. 18, 2015.
Collins, John M., Expert Report—Invalidity, CV14-01645-Appendix I-2-'805, Jun. 18, 2015.
Collins, John M., Expert Report—Invalidity, CV14-01645-Appendix I-3-'805, Jun. 18, 2015.
Collins, John M., Expert Report—Invalidity, CV14-01645-Appendix I-4-'805, Jun. 18, 2015.
Japanese Patent Office, Office Action for JP2011-549417 with English Translation, Jun. 24, 2015.
U.S. Patent and Trademark Office, "Petition for Inter Partes Review", U.S. Patent Trial and Appeal Board, Inter Partes Review No. IPR2015-01578 (Jul. 15, 2015).
U.S. Patent and Trademark Office, "Declaration of Jeffrey Arthur Schuster, Ph.D., under 37 C.F.R. §1.68 in Support of Petitioners Petition for Inter Partes Review of U.S. Pat. No. 8,689,805", U.S. Patent Trial and Appeal Board, Inter Partes Review No. IPR2015-01578 (Jul. 15, 2015).
Korean Intellectual Property Office, "Notice of Final Rejection" issued in Korean Patent Application No. 10-2011-7021209 (Jun. 26, 2015).
European Patent Office, "Search Report" issued in EP Application No. 14155503.7 (Feb. 3, 2015).
European Patent Office, Notice of Opposition to European Patent Application EP10740882.5, Nov. 20, 2015.
Lord, Chris "Declaration of Chris Lord in respect of the public availability of the Loong Totem V9 e-cigarette," undated, 19 pages.
State Intellectual Property Office, Notification of Acceptance of Request for Invalidation for CN200920001296.3, Mar. 3, 2016.

* cited by examiner

ELECTRONIC CIGARETTE

PRIORITY CLAIM

This application is a Continuation of U.S. patent application Ser. No. 13/208,257, filed Aug. 11, 2011, and now pending, which is a continuation of International Application No. PCT/CN2010/000125, filed Jan. 28, 2010, which claims priority to Chinese Patent Application No. 200920001296.3, filed Feb. 11, 2009, all of which are incorporated herein by reference.

TECHNICAL FIELD OF THE INVENTION

The invention relates to an atomizing electric cigarette, in particular to an improved atomizing electric cigarette.

BACKGROUND OF THE INVENTION

As a cigarette substitute, atomizing electronic cigarettes have occupied a large percentage of the market for smoking substitute products, meanwhile, the improvement and maturity of atomizing electronic cigarette technology is a prerequisite for widespread application and acceptance of electronic cigarettes.

At present, the existing atomizing electronic cigarettes still have many problems and shortcomings, for example, poor atomization, large liquid drops in the final atomized smoke, nonuniform smoke caused by different sizes of liquid drops, too much moisture in the smoke, poor mouthfeel, etc. In some conditions, the smoke is at a high temperature because of insufficient cool-down and will cause discomfort.

The above problems cause significant differences between real cigarettes and electronic cigarettes for smokers, which is not conducive for smokers to select electronic cigarettes in place of real ones.

SUMMARY OF THE INVENTION

In order to overcome various shortcomings in the prior art, some embodiments of the invention provide an improved atomizing electronic cigarette having a liquid permeating component in an atomizer that is directly sleeved on an electric heater. Cigarette liquid stored in a liquid storage component permeates into the liquid permeating component. The electric heater directly interacts with the liquid permeating component, such that the cigarette liquid is atomized more sufficiently with smaller and more uniform atomized or vaporized droplets. In another aspect, by communicating through holes and channels provided and arranged in the electric heater and the liquid storage component, the atomized large drops can adhere to the liquid storage component under the pressure of airflow, such that the inhaled smoke is more similar to the feel a real cigarettes to more suitable meet the taste of smoker.

The main technical solution of an embodiment of the invention is as follows: an improved atomizing electronic cigarette is provided, comprising a power supply unit, a sensor, an atomizing core component and a liquid storage component, further comprising a housing containing above components. An auxiliary air inlet is arranged on the housing. One end of the housing is provided with an air suction port. The atomizing core component comprises an electric heater that can atomize liquid from the liquid storage component. The liquid storage component can have an internal channel through which the atomized gas can flow, and the auxiliary air inlet, the sensor and the suction nozzle can form an airflow loop. The through hole through which gas flows can be formed from an internal channel having channel walls in the liquid storage component such that the atomized gas is directly contacted with the core of the liquid storage component through the channel walls, and large particles of atomized gas can be absorbed due to contact with the liquid storage container. Also, the sensor can communicate with the channel to form an airflow loop with the auxiliary air inlet.

The invention also employs the following affiliated technical solution: the atomizing core component comprises a liquid permeating component that is sleeved on an electric heater, a channel or through hole through which gas flows is arranged in the atomizing core component, and the channel or through hole is made up of the structure of the electric heater and liquid permeating component.

The electric heater of the atomizing core component can be directly inserted or stretch directly into the channel of the liquid storage component, such that the atomized gas directly flows through the channel.

The liquid storage component can be internally provided with a hollow channel, a through-hole channel, an annular channel or a cross section of sparse mesh channels or combinations thereof, through which gas flows.

The atomizing core component can further comprise a liquid conduction or transportation component in contact with the liquid permeating component and the liquid storage component.

The liquid conduction or transportation component can be sleeved on the liquid permeating component, and include a conduction part that extends from one end of the liquid conduction component in the radial direction to contact with the liquid storage component.

The sensor can be an air pressure sensor or air flow sensor. The housing can comprise a first housing and a second housing, the power device and the sensor are located in the first housing, the atomizing core component and the liquid storage component are located in the second housing, and the auxiliary air inlet is arranged in an area of the first housing and/or the second housing close to the sensor.

A bracket is arranged in the second housing, where the atomizing core component is fixed on the bracket. The electric heater is connected with the power supply unit and the sensor, and starts to heat or stops heating according to the flow situation of gas through the sensor.

An air-intake connection component and an electrode ring are arranged on the bracket, the air-intake connection component and the electrode ring are electrically connected with two leads of the electric heater respectively. The air-intake connection component achieves electric connection through connection with the sensor. The electrode ring is electrically connected with the power device through the connection of the air-intake connection component and the sensor. The air-intake connection component also has an air vent, and the sensor communicates with the air vent. The through hole and the channel and forms an airflow loop with the auxiliary air inlet.

The first housing and the second housing are joined through the connection of the air-intake connection component and the sensor, and the air-intake connection component and the sensor are connected by means of splicing or plugging, threads, or clamping.

An air suction port is arranged on the second housing, and the sensor communicates with the air vent, the through hole, the channel and the air suction port, and forms an airflow loop with the auxiliary air inlet.

The housing can be an integrated or whole, the front end of which is provided with the auxiliary air inlet, and the sensor communicates with the air vent, the through hole, the channel and the air suction port and forms an airflow loop with the auxiliary air inlet.

The liquid permeating component can be in contact with the liquid storage component. The atomizing core component can be sleeved in the channel of the liquid storage component. The peripheral surface of the liquid permeating component can be mated with the inner wall of the channel.

The liquid storage component can be made of micro-hole ceramic, foamed ceramic, natural fiber, artificial fiber or foam metal material. The liquid permeating component can be made of ceramic fiber, quartz fiber, glass fiber, aramid fiber, common fiber, paper, fabric or non-woven fabric material. The electric heater can be formed by spirally winding electric heating wires or made up of electric heating film arranged on the inner surface of the liquid permeating component, and the electric heater formed by spirally winding or electric heating film on the inner surface of the liquid permeating component can be hollow to form the through hole.

The thickness of the liquid permeating component can be from 0.5 to 5 mm, and the diameter of the through hole can be from 0.5 to 4 mm.

Zeolite particles can be added in the liquid permeating component.

Aspects of the invention can have the following beneficial effects:

(1) the liquid permeating component in the atomizing core component can be directly sleeved on the electric heater such that cigarette liquid in the liquid storage component can permeate into the liquid permeating component. The thickness of the liquid permeating component can be designed to be only 1 mm, such that cigarette liquid permeated in the liquid permeating component can be completely atomized, vaporized or gasified by the electric heater more easily, by for example, when the cigarette liquid in the liquid permeating component is gasified after reaching the boiling point when the electric heater heats. As a result, the gasification of the liquid is more efficient. For example, the drops are smaller and more uniform, having a diameter between 0.04 micrometers to 0.8 micrometers. Such vapor is much more like real cigarette smoke in terms of dispersion degree and appearance. Such vapor is more easily accepted by the pulmonary alveoli and can be absorbed conveniently. Meanwhile, as through holes and channels that are communicated together are arranged in the electric heater and the liquid storage component, atomized gas can pass through the liquid storage component smoothly. And atomized large drops can be absorbed at, or adhere to, the liquid storage component under the pressure of airflow, a common problem in the prior art where vapor having large particles is passed directly to the user. Thus current embodiments produce inhaled smoke that more closely meets the taste of smoker.

(2) In another solution of the some embodiments of the invention, the atomized core component is sleeved in the channel of the liquid storage component, such that the liquid permeating component is directly contacted with the liquid storage component. The cigarette liquid can permeate and conduct more sufficiently and rapidly, to more efficiently produce vapor or atomized smoke. In addition, the structure is simple and saves space, such that the volume of the whole atomizing electronic cigarette can be smaller.

(3) In another embodiment of the invention, the electronic cigarette is designed to be detachable and changeable, such that change of components can be simply achieved by detaching and reassembling the first and second housings. Such an electronic cigarette is more convenient to carry as it is also more portable.

DETAILED DESCRIPTION OF THE INVENTION

Figure 1:
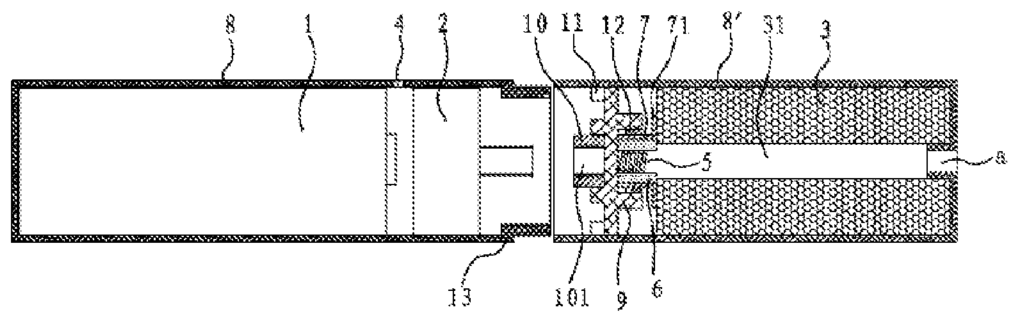
FIG. 1 is a side sectional view of an electronic cigarette according to the invention, showing the first housing separate from the second housing.

The invention will be described in detail below in conjunction with the drawings.

As shown in FIG. 1 to FIG. 5, the invention provides an improved atomizing electronic cigarette, comprising a power device 1, a sensor 2, an atomizing core component and a liquid storage component 3, further comprising a housing containing the above components. An auxiliary air inlet 4 is arranged on an area of the housing close to the sensor 2. The atomizing core component comprises an electric heater 5 and a liquid permeating component 6 sleeved on the electric heater 5. The electric heater 5 is of a hollow structure and has a through hole 51 through which gas flows. The liquid storage component 3 internally has a channel 31 through which the gas flows. The channel can be a hollow channel, a through-hole channel, an annular channel or a channel with local sparse mesh in cross section or combinations thereof, the purpose of which is to make the atomized gas that passes through the channel contact with the liquid storage core of the liquid storage component, and to make the liquid storage component 3 coordinate with the liquid permeating component 6 to permeate cigarette liquid to the liquid permeating component 6. In addition, the sensor 2 communicates with the through hole 51 and the channel 31 and forms an airflow loop with the auxiliary air inlet 4.

Figure 2:
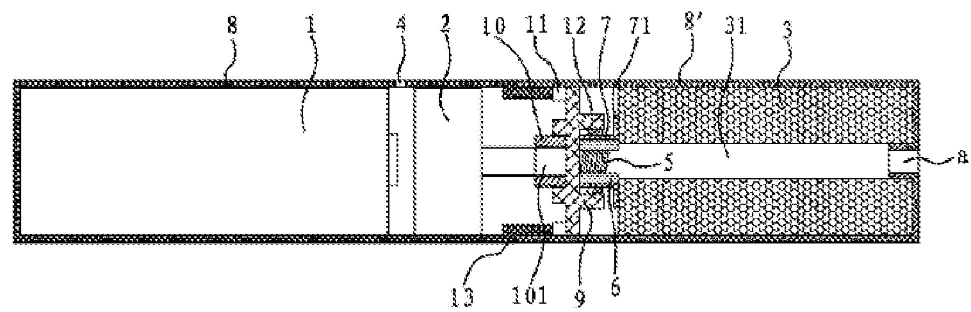
FIG. 2 is a side sectional view of an electronic cigarette according to the invention, showing the first housing connected to the second housing.
Figure 3:
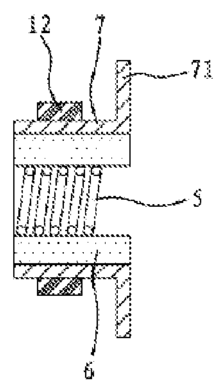
FIG. 3 is a side sectional view of an atomizing core component in an electronic cigarette according to the invention.

In the embodiment, as shown in FIG. 1 to FIG. 3, the atomizing core component further comprises a liquid conduction component 7 that is contacted with the liquid permeating component 6 and with the liquid storage component 3. The liquid conduction component 7 is sleeved on the liquid permeating component 6, with a conduction part 71 that extends from one end of the liquid conduction component in the radial direction, and is contacted with the liquid storage component 3. As a result, cigarette liquid on the liquid storage component 3 is absorbed and permeated to the liquid permeating component. In order to make the liquid conduction component 7 mate with the liquid permeating component 6 more tightly to improve the liquid conductivity, a fastening sleeve 12 can be sleeved on the liquid conduction component 7.

As shown in FIG. 1, the sensor 2 can be an air pressure sensor or airflow sensor. In the embodiment, an airflow sensor is used. The housing comprises a first housing 8 and a second housing 8', the power supply unit 1 and the sensor 2 are located in the first housing 8, the atomizing core component and the liquid storage component 3 are located in the second housing 8', and the auxiliary air inlet 4 is arranged in an area of the first housing 8 and/or the second housing 8' close to the sensor 2. In the embodiment, the auxiliary air inlet 4 is arranged on the first housing 8 and located in an area close to the sensor 2. The power supply unit 1 is a battery that can be a rechargeable battery or disposable battery.

Figure 4:
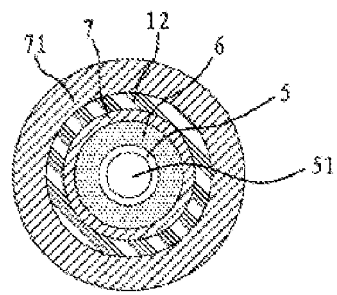
FIG. 4 is a top view of an atomizing core component in an electronic cigarette according to the invention.
Figure 5:
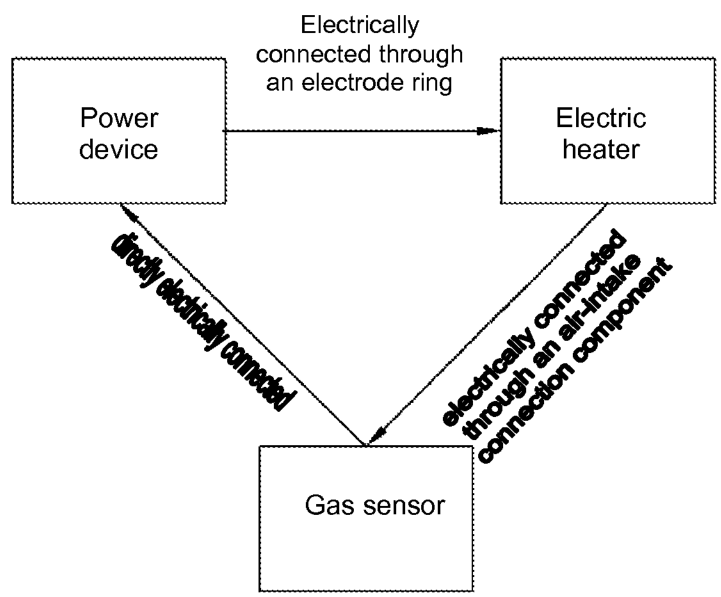
FIG. 5 is an electrical connection block diagram for forming a closed loop among components of an electronic cigarette according to the invention.

A bracket 9 is arranged in the second housing 8', the atomizing core component is fixed on the bracket 9, and the electric heater 5 is connected with the power device 1 and the sensor 2 and starts to heat or stops heating according to the flow situation of gas detected by the sensor 2. An air-intake connection component 10 and an electrode ring 11 are arranged on the bracket 9. The air-intake connection component 10 and the electrode ring 11 are electrically connected with two leads of the electric heater 5, respectively. The air-intake connection component 10 achieves an electrical connection through connection with the sensor 2. The electrode ring 11 is electrically connected with the power device 1 through the connection of the air-intake connection component 10 and the sensor 2. A complete closed loop is formed, as shown in FIG. 4. The function of the sensor is to switch on or off the whole circuit according to the gas flow. When user inhales, gas inside the electronic cigarette flows. At this time, the sensor switches the circuit on to start the electric heater 5 to heat. When the user stops inhaling, gas stops flowing, and the sensor switches the circuit off to make the electric heater 5 stop heating. An electrode ring post 13 corresponding to the electrode ring 10 is arranged at the opening of the first housing 8. A contact part 131 extends from the electrode ring post 13 in the axial direction. The electrode ring post 13 is connected with the power device 1. When the first housing 8 and the second housing 8' are connected, the contact part 131 is inserted into the second housing 8' and contacted with the electrode ring 11, thereby to form a complete closed loop.

In this embodiment, the first housing 8 and the second housing 8' are connected through the connection of the air-intake connection component 10 and the sensor 2, and the air-intake connection component 10 and the sensor 2 are connected by means of splicing or plugging, threads, or clamping. Through such a detachable and changeable split structure, the change of components can be simply achieved by detaching and reassembling the first housing 8 and the second housing 8', such that it is convenient to carry and use the electronic cigarette. This embodiment discloses a connection structure by means of threads.

As shown in FIG. 1, the air-intake connection component 10 also has an air vent 101, the sensor 2 communicates with the air vent 101, the through hole 51 and the channel 31 and forms an airflow loop with the auxiliary air inlet 4. An air suction port a is arranged on the second housing 8', and the sensor 2 communicates with the air vent 101, the through hole 51, the channel 31 and the air suction port a and forms an airflow loop with the auxiliary air inlet 4.

The liquid storage component 3 is made of liquid storage core materials such as micro-hole ceramic, foamed ceramic, natural fiber, artificial fiber or foam metal material. The liquid permeating component 6 is made of ceramic fiber, quartz fiber, glass fiber, aramid fiber, common fiber, paper, fabric or non-woven fabric material. The thickness of the liquid permeating component 6 is from 0.5 to 5 mm. The electric heater 5 is formed by spirally winding electric heating wires, which forms the through hole 51. The diameter of the through hole 51 can be from 0.5 to 4 mm. In this embodiment, the thickness of the liquid permeating component 6 is 1 mm, and the diameter of the through hole 51 is 1 mm.

The liquid permeating component 6 in the atomizing core component is directly sleeved on the electric heater 5. Cigarette liquid in the liquid storage component 3 is conducted and permeated to the liquid permeating component 6 by the liquid conduction component 7. The thickness of the liquid permeating component 6 is 1 mm. As a result, the permeated cigarette liquid can be completely gasified by the electric heater 5 more easily. When the user inhales, as the sensor 2 communicates with the air vent 101, the through hole 51, the channel 31 and the air suction port a and forms an airflow loop with the auxiliary air inlet 4. When gas flow is generated inside the electronic cigarette, the sensor 3 switches the circuit on, the electric heater 5 starts to heat to make the cigarette liquid in the liquid permeating component 6 be gasified after reaching the boiling point. At the same time, because the through hole 51 and the channel 31 of the electric heater 5 and the liquid storage component 3 are in communication, smoke generated during atomizing process can be further cooled under the push of airflow and finally inhaled to the mouth cavity of the user through the air suction port a.

Figure 6:
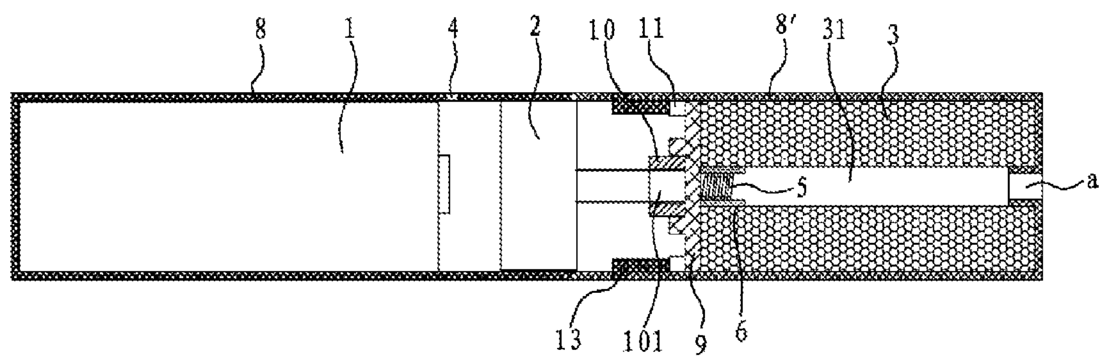
FIG. 6 is a side cutaway view of an electronic cigarette according to another embodiment of the invention.

In another preferred embodiment of the invention, as shown in FIG. 6, the liquid permeating component 6 is contacted with the liquid storage component 3. The atomizing core component is sleeved in the channel 31 of the liquid storage component 3, and the peripheral surface of the liquid permeating component 6 is mated with the inner wall of the channel 31.

The liquid storage component 3 can be made of micro-hole ceramic, foamed ceramic, natural fiber, artificial fiber or foam metal material. The liquid permeating component 6 can be made of ceramic fiber, quartz fiber, glass fiber, aramid fiber, common fiber, paper, fabric or non-woven fabric material. The thickness of the liquid permeating component 6 ranks from 0.5 to 5 mm. The electric heater 5 is formed by spirally winding electric heating wires to form a through hole 51. The diameter of the through hole 51 can be from 0.5 to 4 mm. In this embodiment, the thickness of the liquid permeating component 6 is 1 mm and the diameter of the through hole 51 is 1 mm.

In this embodiment, the atomizing core component is integrally sleeved in the channel 31 of the liquid storage component 3, such that the spherical surface of the liquid permeating component 6 is directly contacted with the inner wall of the channel 31 of the liquid storage component 3. Because the contact area is larger, the permeation and conduction of cigarette liquid is more sufficient and rapid, and the atomized smoke efficiently generated. At the same time, the structure is simple and saves space, so as to minimize the size of the atomizing electronic cigarette.

In other embodiments, an improved atomizing electronic cigarette is provided comprising a power device (1), a sensor (2), an atomizing core component and a liquid storage component (3), further comprising a housing containing the above components, an auxiliary air inlet (4) being arranged on the housing. One end of the housing is provided with an air suction port, characterized in that the atomizing core component comprises an electric heater (5), the electric heater (5) atomizes liquid in a liquid storage component (3). The liquid storage component (3) internally has a channel (31) through which the atomized gas flows, and the auxiliary air inlet (4), the sensor (2) and the suction nozzle form an airflow loop.

In other aspects the atomizing electronic cigarette can be characterized in that the atomizing core component comprises a liquid permeating component (6) that is sleeved on the electric heater (5), a channel (51) through which gas flows is arranged in the atomizing core component, and the channel (51) is made up of the structure of the electric heater (5).

In other aspects the atomizing electronic cigarette can be characterized in that the electric heater (5) of the atomizing core component is directly inserted into the channel (31) of the liquid storage component (3), and the atomized gas directly flows through the channel (31).

In other aspects the atomizing electronic cigarette is characterized in that the liquid storage component (3) is internally provided with the channel (31) which is a hollow channel, a through-hole channel, an annular channel or a channel with local sparse mesh in cross section or combinations thereof, through which gas flows.

In other aspects the atomizing electronic cigarette is characterized in that the atomizing core component further comprises a liquid conduction component (7) that is contacted with the liquid permeating component (6), and with the liquid storage component (3).

In other aspects, the atomizing electronic cigarette is characterized in that the liquid conduction component (7) is sleeved on the liquid permeating component (6), a conduction part (71) extends from one end of the liquid conduction component in the radial direction, and the conduction part (71) is contacted with the liquid storage component (3).

In other aspects, the atomizing electronic cigarette is characterized in that the sensor (2) is an air pressure sensor or airflow sensor, the housing comprises a first housing (8) and a second housing (8'), the power device (1) and the sensor (2) are located in the first housing (8), the atomizing core component and the liquid storage component (3) are located in the second housing (8'), and the auxiliary air inlet (4) is arranged in an area of the first housing (8) and/or the second housing (8') close to the sensor.

In other aspects, the atomizing electronic cigarette is characterized in that a bracket (9) is arranged in the second housing (8'), the atomizing core component is fixed on the bracket (9), and the electric heater (5) is connected with the power device (1) and the sensor (2) and starts to heat or stops heating according to the flow situation of gas through the sensor (2).

In other aspects, the atomizing electronic cigarette is characterized in that an air-intake connection component (10) and an electrode ring (11) are arranged on the bracket (9), the air-intake connection component (10) and the electrode ring (11) are electrically connected with two leads of the electric heater (5) respectively, the air-intake connection component (10) achieves electric connection through connection with the sensor (2), the electrode ring (11) is electrically connected with the power device (1) through the connection of the air-intake connection component (10) and the sensor (2), the air-intake connection component (10) also has an air vent (101), the sensor (2) communicates with the air vent (101), the through hole (51) and the channel (31) and forms an airflow loop with the auxiliary air inlet (4).

In other aspects, the atomizing electronic cigarette is characterized in that the first housing (8) and the second housing (8') are connected through the connection of the air-intake connection component (10) and the sensor (2), and the air-intake connection component (10) and the sensor (2) are connected by means of splicing or plugging, threads or clamping.

In other aspects, the atomizing electronic cigarette is characterized in that an air suction port (a) is arranged on the second housing (8'), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the housing is an integrated whole, the front end of which is provided with the auxiliary air inlet (4), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the liquid permeating component (6) is contacted with the liquid storage component (3), the atomizing core component is sleeved in the channel (31) of the liquid storage component (3), and the peripheral surface of the liquid permeating component (6) is mated with the inner wall of the channel (31).

In other aspects, the atomizing electronic cigarette is characterized in that the liquid storage component (3) is made of micro-hole ceramic, foamed ceramic, natural fiber, artificial fiber or foam metal material, the liquid permeating component (6) is made of ceramic fiber, quartz fiber, glass fiber, aramid fiber, common fiber, paper, fabric or non-woven fabric material, the electric heater (5) is formed by spirally winding electric heating wires or made up of electric heating film arranged on the inner surface of the liquid permeating component, and the electric heater formed by spirally winding or electric heating film on the inner surface of the liquid permeating component is hollow to form the through hole (51).

In other aspects, the atomizing electronic cigarette is characterized in that the thickness of the liquid permeating component (6) ranks from 0.5 to 5 mm, and the diameter of the through hole (51) ranks from 0.5 to 4 mm.

In other aspects, the atomizing electronic cigarette is characterized in that zeolite particles are added in the liquid permeating component (6).

The invention claimed is:

1. An electronic cigarette, comprising:

a housing;

a battery, and a liquid storage component containing liquid, within the housing;

a wire coil electrically connectable to the battery for atomizing liquid from the liquid storage component, with the wire coil surrounded by the liquid storage component;

a channel extending centrally through the liquid storage component, with the wire coil in the channel and having a diameter less than the channel; and the channel forming part of an airflow path within the housing providing a continuous passageway from the wire coil to an inhalation port, and the channel having a uniform diameter between the wire coil and the inhalation port.

2. The electronic cigarette of claim 1 further including a porous component surrounding and in contact with the wire coil, and the liquid storage component surrounding the porous component.

3. The electronic cigarette of claim 2 with the porous component longer than the wire coil.

4. The electronic cigarette of claim 1 with the channel having internal surfaces wetted via the liquid, for cooling vapor flowing through the channel.

5. The electronic cigarette of claim 1 with the airflow path centrally located within the housing.

6. The electronic cigarette of claim 1 with the liquid storage component comprising a fiber material.

7. The electronic cigarette of claim 6 with the channel formed as an opening through the fiber material.

8. The electronic cigarette of claim 1 with the liquid storage component comprising a hollow elongated cylinder having an annular cross section co-axial with the channel.

9. The electronic cigarette of claim 1 wherein the channel is cylindrical.

10. An electronic cigarette, comprising:

a housing having an inhalation port;

a battery and a liquid storage component within the housing, with the liquid storage component comprising a fiber material and holding a liquid;

an electric heater comprising a wire coil in the housing connectable to the battery for creating vapor from liquid provided from the liquid storage component; and an open cylindrical channel through the fiber material of the liquid storage component from a first end of the liquid storage component to a second end of the liquid storage component, the channel having surfaces wetted via the liquid, and with the wire coil in the channel and the wire coil having a diameter less than the channel, and the channel providing a continuous passageway from the wire coil to the inhalation port.

11. The electronic cigarette of claim 10 with the channel having a uniform diameter between the wire coil to the inhalation port.

12. The electronic cigarette of claim 10 with the wetted internal surfaces of the channel cooling vapor flowing through the channel.

13. The electronic cigarette of claim 12 with the liquid storage component comprising a fiber material.

14. The electronic cigarette of claim 10 with the liquid storage component comprising a hollow elongated cylinder having an annular cross section.

15. An electronic cigarette, comprising:

a housing;

a battery, and a liquid storage component holding a liquid, within the housing, and the liquid storage component comprising a hollow elongated cylinder having an annular cross section;

a wire coil electrically connected to the battery for atomizing liquid from the liquid storage component, with the wire coil surrounded by the liquid storage component;

a cylindrical central channel through the liquid storage component having surfaces wetted via the liquid, with the wire coil in the channel and having a diameter less than the channel; and the channel forming part of an airflow path within the housing, and the channel providing a continuous and open passageway from the wire coil to an inhalation port, and the channel having a uniform diameter between the wire coil and the inhalation port.

16. The electronic cigarette of claim 15 with the liquid storage component comprising a fiber material.

* * * * *